(12) United States Patent
Koyakumaru et al.

(10) Patent No.: US 7,524,967 B2
(45) Date of Patent: Apr. 28, 2009

(54) PROCESS FOR PRODUCING 5-(2'-PYRIDYL)-2-PYRIDONE DERIVATIVE

(75) Inventors: Kenichi Koyakumaru, Bizen (JP); Yoshimi Fukunaga, Chiyoda-ku (JP); Youichi Satake, Kurashiki (JP)

(73) Assignees: Kuraray Co., Ltd., Kurashiki-shi (JP); Eisai R & D Management Co., Ltd., Tokyo (JP)

( * ) Notice: Subject to any disclaimer, the term of this patent is extended or adjusted under 35 U.S.C. 154(b) by 627 days.

(21) Appl. No.: 10/521,800

(22) PCT Filed: Jul. 23, 2003

(86) PCT No.: PCT/JP03/09316

§ 371 (c)(1), (2), (4) Date: Aug. 2, 2005

(87) PCT Pub. No.: WO2004/009553

PCT Pub. Date: Jan. 29, 2004

(65) Prior Publication Data

US 2006/0004205 A1 Jan. 5, 2006

(30) Foreign Application Priority Data

Jul. 23, 2002 (JP) ............................. 2002-214098

(51) Int. Cl.
*C07D 401/04* (2006.01)

(52) U.S. Cl. ................................................ 546/257

(58) Field of Classification Search ........................ None
See application file for complete search history.

(56) References Cited

U.S. PATENT DOCUMENTS

| 5,693,611 | A | 12/1997 | Henle et al. |
| 6,169,184 | B1 | 1/2001 | Hamprecht et al. |
| 6,949,571 | B2 * | 9/2005 | Nagato et al. ............... 514/334 |

FOREIGN PATENT DOCUMENTS

| JP | 2000-80082 | 3/2000 |
| WO | 98/07700 | 2/1998 |
| WO | 01/27112 | 4/2001 |
| WO | 01/81310 | 11/2001 |
| WO | 01/96308 | 12/2001 |

OTHER PUBLICATIONS

Bonnet, Veronique et al. "Syntheses of substituted pyridines, quinolines and diazines via palladium-catalyzed cross-coupling of aryl Grignard reagents", Tetrahedron, vol. 58, No. 22, pp. 4429-4438.

(Continued)

*Primary Examiner*—Zinna N Davis
(74) *Attorney, Agent, or Firm*—Oblon, Spivak, McClelland, Maier & Neustadt, P.C.

(57) ABSTRACT

The present invention provides a method of industrially and advantageously producing a 5-(2'-pyridyl)-2-pyridone derivative. The present invention relates to a production method of a 5-(2'-pyridyl)-2-pyridone derivative represented by the formula (VI), which includes reacting a pyridine derivative of the formula (I) with a brominating agent to give a 5-bromopyridine derivative of the formula (II), reacting the obtained 5-bromopyridine derivative with a metallizing agent to give an organometallic compound of the formula (III), reacting the obtained organometallic compound with a 2-sulfonylpyridine derivative of the formula (IV) to give a 6-alkoxy-3,2'-bipyridine derivative of the formula (V) and hydrolyzing the obtained 6-alkoxy-3,2'-bipyridine derivative:

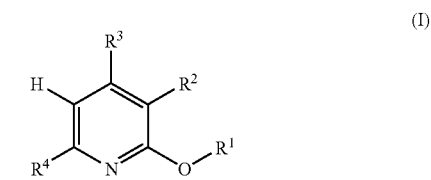

(I)

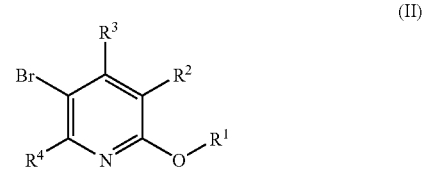

(II)

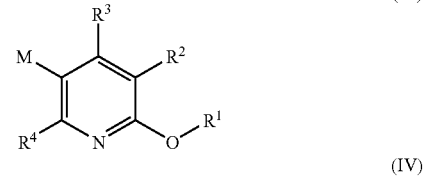

(III)

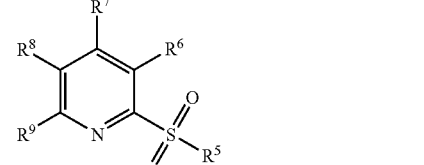

(IV)

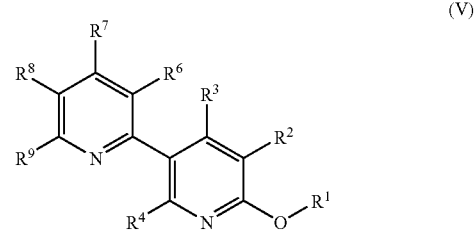

(V)

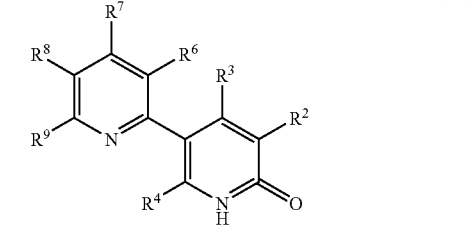

(VI)

wherein each symbol is as defined in the Description.

18 Claims, No Drawings

OTHER PUBLICATIONS

Heirtzler, Fenton R. et al. "Preparation and Characterization of Oligo-(2,2'-bipyridyl)pyrazines", Liebigs Ann./Recueil, pp. 297-301 1997.

Wakabayashi, Shoji et al. "A Cross-Coupling Reaction of Methylsulfinylarene", Bull. Chem. Soc. Jpn., vol. 62, No. 12, pp. 3848-3850 1989.

John R. Proudfoot, et al. "Novel Non-Nucleoside Inhibitors of Human Immunodeficiency Virus Type 1 (HIV-1) Reverse Transcriptase. 4.[1] 2-Substituted Dipyridodiazepinones as Potent Inhibitors of Both Wild-Type and Cysteine-181 HIV-1 Reverse Transcriptase Enzymes", Journal of Medicinal Chemistry, XP-002031262, vol. 38, No. 24, 1995, pp. 4830-4838.

* cited by examiner

PROCESS FOR PRODUCING 5-(2'-PYRIDYL)-2-PYRIDONE DERIVATIVE

TECHNICAL FIELD

The present invention relates to a production method of a 5-(2'-pyridyl)-2-pyridone derivative. The 5-(2'-pyridyl)-2-pyridone derivative obtained by the present invention is useful as an intermediate for a therapeutic drug for nervous diseases (WO01-96308).

BACKGROUND ART

Conventionally, as a method of producing a 3,2'-bipyridine derivative having an oxygen functional group at the 6-position, (1) a method comprising reacting a 2-alkoxypyridine derivative, wherein the 5-position is substituted by a boron atom, a tin atom and the like, with a 2-halogenated pyridine derivative in the presence of a palladium catalyst (WO2001-81310, U.S. Pat. No. 5,693,611), and (2) a method comprising reacting a pyridine derivative, wherein the 2-position is substituted by a boron atom, a tin atom and the like, with 5-halogenated 2-alkoxypyridine in the presence of a palladium catalyst (WO2001-96308, WO2001-27112) are known.

Both the above-mentioned methods (1) and (2) are expensive and require use of a palladium catalyst whose waste liquid has a pollution problem, which inevitably increases the cost, and cannot be employed industrially.

DISCLOSURE OF THE INVENTION

It is an object of the present invention to provide a method capable of producing a 5-(2'-pyridyl)-2-pyridone derivative industrially advantageously.

The present invention relates to

[1] a production method of a 5-(2'-pyridyl)-2-pyridone derivative represented by the formula (VI)

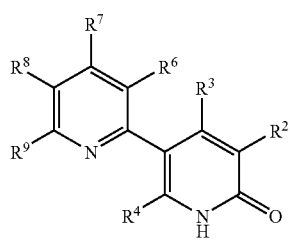

(VI)

wherein $R^2$, $R^3$ and $R^4$ are each a hydrogen atom, an alkyl group optionally having substituent(s), an aryl group optionally having substituent(s), an alkoxy group optionally having substituent(s) or an aryloxy group optionally having substituent(s), or $R^2$ and $R^3$ optionally form, together with a carbon atom bonded thereto, a ring optionally having substituent(s), and $R^6$, $R^7$, $R^8$ and $R^9$ are each a hydrogen atom, an alkyl group optionally having substituent(s) or an aryl group optionally having substituent(s), or $R^6$ and $R^7$, $R^7$ and $R^8$, or $R^8$ and $R^9$ optionally form, together with a carbon atom bonded thereto, a ring optionally having substituent(s)

[hereinafter to be abbreviated as 5-(2'-pyridyl)-2-pyridone derivative (VI)], which comprises reacting a pyridine derivative represented by the formula (I)

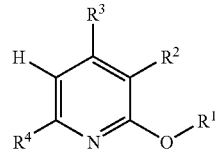

(I)

wherein $R^1$ is an alkyl group optionally having substituent(s) or an aryl group optionally having substituent(s), and $R^2$, $R^3$ and $R^4$ are as defined above [hereinafter to be abbreviated as pyridine derivative (I)] with a brominating agent to give a 5-bromopyridine derivative represented by the formula (II)

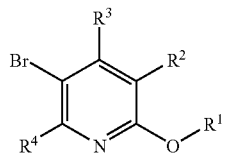

(II)

wherein $R^1$, $R^2$, $R^3$ and $R^4$ are as defined above [hereinafter to be abbreviated as 5-bromopyridine derivative (II)], reacting the obtained 5-bromopyridine derivative (II) with a metallizing agent to give an organometallic compound represented by the formula (III)

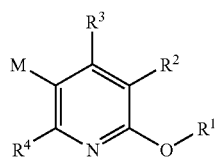

(III)

wherein M is a metal atom belonging to group 1 of the periodic table, and $R^1$, $R^2$, $R^3$ and $R^4$ are as defined above [hereinafter to be abbreviated as organometallic compound (III)], reacting the obtained organometallic compound (III) with a 2-sulfonylpyridine derivative represented by the formula (IV)

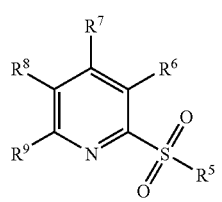

(IV)

wherein $R^5$ is an alkyl group optionally having substituent(s) or an aryl group optionally having substituent(s), and $R^6$, $R^7$, $R^8$ and $R^9$ are as defined above [hereinafter to be abbreviated as 2-sulfonylpyridine derivative (IV)], to give a 6-alkoxy-3,2'-bipyridine derivative represented by the formula (V)

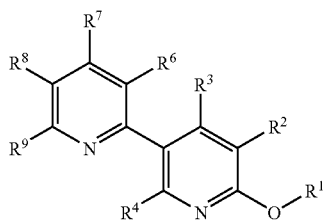

wherein $R^1$, $R^2$, $R^3$, $R^4$, $R^6$, $R^7$, $R^8$ and $R^9$ are as defined above [hereinafter to be abbreviated as 6-alkoxy-3,2'-bipyridine derivative (V)], and hydrolyzing the obtained 6-alkoxy-3,2'-bipyridine derivative (V),

[2] the production method of the above-mentioned [1], wherein the organometallic compound is a compound of the formula (III) wherein M is a lithium atom,

[3] the production method of the above-mentioned [1] or [2], wherein, in the formula (VI), $R^2$, $R^3$, $R^4$, $R^6$, $R^7$, $R^8$ and $R^9$ are each a hydrogen atom,

[4] the production method of [1] or [2] above, wherein, in the formula (I), $R^1$ is a methyl group,

[5] the production method of [1] or [2], wherein, in the formula (IV), $R^5$ is a phenyl group,

[6] the production method of [1], wherein the metallizing agent is an n-butyllithium,

[7] the production method of [1], wherein the brominating agent is a bromine, and

[8] the production method of [1], wherein $R^2$, $R^3$, $R^4$, $R^5$, $R^6$, $R^7$ and $R^9$ of the formula (VI) are each a hydrogen atom;

$R^1$ of the formula (I) is a methyl group;

the brominating agent is a bromine;

the metallizing agent is an n-butyllithium;

the organometallic compound is a compound of the formula (III) wherein M is a lithium atom; and $R^5$ of the formula (IV) is a phenyl group.

DETAILED DESCRIPTION OF THE INVENTION

In the above-mentioned formulas, the alkyl group represented by each of $R^1$, $R^2$, $R^3$, $R^4$, $R^5$, $R^6$, $R^7$, $R^8$ and $R^9$ and the alkyl group possessed by the alkoxy group represented by each of $R^2$, $R^3$ and $R^4$ may be linear, branched or cyclic, and preferably has 1 to 12 carbon atoms. As the alkyl group, for example, methyl group, ethyl group, propyl group, isopropyl group, butyl group, isobutyl group, tert-butyl group, hexyl group, octyl group, dodecyl group, cyclopentyl group, cyclohexyl group and the like can be mentioned. The ring optionally formed by $R^2$ and $R^3$, $R^6$ and $R^7$, $R^7$ and $R^8$, or $R^8$ and $R^9$, together with a carbon atom bonded thereto, is not particularly limited, and, for example, an aliphatic hydrocarbon ring and the like can be mentioned. The ring preferably has 4 to 10 carbon atoms. As the ring, for example, cyclopentane ring, cyclohexane ring, cycloheptane ring, cyclodecan ring and the like can be mentioned.

The above-mentioned alkyl group and ring optionally have substituent(s). As the substituent, for example, aryl group having 4 to 15 carbon atoms such as phenyl group, tolyl group, methoxyphenyl group, chlorophenyl group, bromophenyl group, nitrophenyl group, naphthyl group, anthracenyl group, pyridyl group, furyl group, thienyl group and the like, which optionally has a hetero atom such as nitrogen atom, oxygen atom, sulfur atom and the like in a ring structure, and preferably comprises 5 to 14 ring members; an alkenyl group having 2 or 3 carbon atoms such as vinyl group, 1-methylvinyl group and the like; a halogen atom such as fluorine atom, chlorine atom, bromine atom, iodine atom and the like; a linear, branched or cyclic alkoxy group having 1 to 12 carbon atoms, such as methoxy group, ethoxy group, propoxy group, isopropoxy group, butoxy group, isobutoxy group, tert-butoxy group, hexyloxy group, octyloxy group, dodecyloxy group, cyclopentyloxy group, cyclohexyloxy group, allyloxy group, benzyloxy group and the like; an aryloxy group having 4 to 15 carbon atoms such as phenoxy group, chlorophenoxy group, bromophenoxy group, nitrophenoxy group, naphthyloxy group, anthracenyloxy group, pyridyloxy group, furyloxy group, thienyloxy group and the like, which optionally has a hetero atom such as nitrogen atom, oxygen atom, sulfur atom and the like in a ring structure, and preferably comprises 5 to 14 ring members, and the like can be mentioned.

As representative examples of alkoxy group optionally having substituent(s) for $R^2$, $R^3$ or $R^4$, methoxy group, ethoxy group, propoxy group, isopropoxy group, butoxy group, isobutoxy group, tert-butoxy group, hexyloxy group, octyloxy group, cyclopentyloxy group, cyclohexyloxy group, allyloxy group, benzyloxy group and the like can be mentioned.

The aryl group represented by each of $R^1$, $R^2$, $R^3$, $R^4$, $R^5$, $R^6$, $R^7$, $R^8$ and $R^9$, and the aryl group possessed by the aryloxy group represented by each of $R^2$, $R^3$ and $R^4$ optionally have a hetero atom such as nitrogen atom, oxygen atom, sulfur atom and the like in a ring structure, and preferably have 4 to 15 carbon atoms. The number of ring members is preferably 5 to 14. As the aryl group, for example, phenyl group, naphthyl group, anthracenyl group, pyridyl group, furyl group, thienyl group and the like can be mentioned.

The above-mentioned aryl group optionally has substituent(s). As the substituent, for example, a linear, branched or cyclic alkyl group having 1 to 12 carbon atoms, such as methyl group, ethyl group, propyl group, isopropyl group, butyl group, isobutyl group, tert-butyl group, hexyl group, octyl group, dodecyl group, cyclopentyl group, cyclohexyl group and the like; an aryl group having 4 to 15 carbon atoms such as phenyl group, tolyl group, methoxyphenyl group, chlorophenyl group, bromophenyl group, nitrophenyl group, naphthyl group, anthracenyl group, pyridyl group, furyl group, thienyl group and the like, which optionally has a hetero atom such as nitrogen atom, oxygen atom, sulfur atom and the like in a ring structure, and preferably comprises 5 to 14 ring members; a halogen atom such as fluorine atom, chlorine atom, bromine atom, iodine atom and the like; a linear, branched or cyclic alkoxy group having 1 to 12 carbon atoms, such as methoxy group, ethoxy group, propoxy group, isopropoxy group, butoxy group, isobutoxy group, tert-butoxy group, hexyloxy group, octyloxy group, dodecyloxy group, cyclopentyloxy group, cyclohexyloxy group, allyloxy group, benzyloxy group and the like; an aryloxy group having 4 to 15 carbon atoms such as phenoxy group, chlorophenoxy group, bromophenoxy group, nitrophenoxy group, naphthyloxy group, anthracenyloxy group, pyridyloxy group, furyloxy group, thienyloxy group and the like, which optionally has a hetero atom such as nitrogen atom, oxygen atom, sulfur atom and the like in a ring structure, and preferably comprises 5 to 14 ring members, and the like can be mentioned.

As representative examples of aryloxy group represented by $R^2$, $R^3$ or $R^4$, phenoxy group, chlorophenoxy group, bromophenoxy group, nitrophenoxy group, naphthyloxy group, pyridyloxy group, furyloxy group, thienyloxy group and the like can be mentioned.

First, a step for reacting pyridine derivative (I) with a brominating agent is explained.

As the brominating agent, for example, bromine, bromine-pyridine complex, dimethyldibromohydantoin and the like can be mentioned, and bromine is particularly preferable. The amount of the brominating agent to be used is preferably within the range of 0.1 to 10 molar equivalents, more preferably 0.5 to 3 molar equivalents, relative to pyridine derivative (I).

The reaction is preferably carried out within the range of −20° C. to 100° C., more preferably 0 to 80° C. The reaction time is within the range of generally 0.1 to 40 hr, preferably 0.5 to 20 hr.

The reaction can be carried out by, for example, mixing pyridine derivative (I) with a brominating agent in a solvent in the presence of a base. The solvent is not particularly limited as long as it does not influence the reaction. For example, esters such as ethyl acetate, isopropyl acetate, butyl acetate and the like; nitriles such as acetonitrile, benzonitrile and the like; aliphatic hydrocarbons such as hexane, heptane, octane and the like; halogenated hydrocarbons such as dichloromethane, 1,2-dichloroethane, chlorobenzene and the like; organic carboxylic acids such as acetic acid, propionic acid and the like; and the like can be mentioned. The solvent may be used alone or in a combination of two or more kinds thereof. The amount of the solvent to be used is generally within the range of 0.5- to 50-fold weight, preferably 1- to 20-fold weight, relative to pyridine derivative (I).

The reaction can be carried out in the presence of a base. As the base, for example, inorganic bases such as lithium hydroxide, sodium hydroxide, potassium hydroxide, lithium carbonate, sodium carbonate, potassium carbonate, sodium hydrogencarbonate and the like; organic carboxylic acid alkali metal salts such as lithium acetate, sodium acetate, potassium acetate and the like; tertiary amines such as pyridine, picoline, lutidine, triethylamine, tributylamine, trioctylamine and the like; and the like can be mentioned. Of these, sodium carbonate, potassium carbonate, sodium acetate and potassium acetate are preferable, and sodium acetate and potassium acetate are particularly preferable. The amount of the base to be used is preferably within the range of 0.1 to 10 molar equivalents, more preferably within the range of 0.5 to 3 molar equivalents, relative to pyridine derivative (I).

The 5-bromopyridine derivative (II) obtained in this step is preferably used in the next reaction after isolation or purification. The 5-bromopyridine derivative (II) is isolated or purified from the reaction mixture by the methods generally used for the isolation or purification of organic compounds. For example, a brominating agent remaining in the reaction mixture is decomposed using sodium sulfite and the like, the reaction mixture is neutralized with sodium hydroxide and the like until the system becomes alkaline, then the mixture is extracted by adding an organic solvent such as ethyl acetate and the like, the extract is concentrated and the obtained crude product is purified by distillation, recrystallization, silica gel chromatography and the like.

Secondly, a step of reacting 5-bromopyridine derivative (II) with a metallizing agent and a step of reacting organometallic compound (III) with a 2-sulfonylpyridine derivative (IV) are explained.

As the metallizing agent, for example, alkyllithium compounds such as methyllithium, n-butyllithium and the like; Grignard reagents such as ethyl magnesium bromide, isopropyl magnesium bromide, isopropyl magnesium chloride, t-butyl magnesium chloride and the like; and metals such as lithium, magnesium, sodium and the like can be mentioned. The amount of the metallizing agent to be used is preferably within the range of 0.1 to 10 molar equivalents, more preferably 0.5 to 3 molar equivalents, relative to 5-bromopyridine derivative (II).

The reactions in the both steps are preferably carried out in the presence of a solvent. While the solvent is not particularly limited as long as it does not adversely affect the reaction, for example, aliphatic hydrocarbons such as hexane, heptane, octane and the like; aromatic hydrocarbons such as benzene, toluene, xylene, ethylbenzene, mesitylene and the like; ethers such as tetrahydrofuran, diethyl ether, diisopropyl ether, tert-butylmethyl ether, 1,2-dimethoxyethane, 1,4-dioxane, diglyme and the like; and the like can be mentioned. Of these, ether is preferably used and tetrahydrofuran is particularly preferably used. The solvent may be used alone or in a combination of two or more kinds thereof.

The reaction between 5-bromopyridine derivative (II) and a metallizing agent is preferably carried out within the range of −100° C. to 100° C., more preferably −80° C. to 80° C. The reaction time is generally within the range of 0.1-40 hr, preferably 0.5-20 hr. The amount of the solvent to be used in this reaction is generally within the range of 0.5- to 50-fold weight, preferably 1- to 20-fold weight, relative to 5-bromopyridine derivative (II).

The step of reacting 5-bromopyridine derivative (II) with a metallizing agent can be performed by, for example, mixing 5-bromopyridine derivative (II) with a metallizing agent in the above-mentioned solvent.

After the completion of the reaction, the reaction mixture containing organometallic compound (III) can be used in the next reaction step.

The amount of the organometallic compound (III) to be used is generally within the range of 0.1 to 10 equivalents, more preferably 0.5 to 3 equivalents, relative to 2-sulfonylpyridine derivative (IV).

The reaction between organometallic compound (III) and 2-sulfonylpyridine derivative (IV) is preferably carried out within the range of −100 to 100° C., more preferably −80° C. to 50° C. The reaction time is within the range of generally 0.1-40 hr, preferably 0.5-20 hr. The amount of the solvent to be used is generally within the range of 0.5- to 100-fold weight, preferably 1- to 20-fold weight, relative to 2-sulfonylpyridine derivative (IV).

As for the operation for the reaction, 2-sulfonylpyridine derivative (IV) is added to a reaction mixture containing the above-mentioned organometallic compound (III), or a reaction mixture containing the above-mentioned organometallic compound (III) is added to a solution of 2-sulfonylpyridine derivative (IV). Before addition, 2-sulfonylpyridine derivative (IV) may be diluted with the above-mentioned reaction solvent. While the concentration after dilution is not particularly limited, 2-sulfonylpyridine derivative (IV) preferably has a concentration within the range of 1-80 wt %, more preferably 5-50 wt %. While the rate of addition is not particularly limited, it is preferably such speed that enables control of the temperature to a level to obtain a good reaction result.

6-Alkoxy-3,2'-bipyridine derivative (V) obtained in this step can be used for the next reaction without isolation and purification. For example, a reaction mixture is added to water, the mixture is extracted by adding an organic solvent such as ethyl acetate and the like, the extract is concentrated and the obtained crude product is subjected to the next reaction step.

A step for hydrolysis of 6-alkoxy-3,2'-bipyridine derivative (V) is now explained in the following.

The hydrolysis reaction is preferably carried out in the presence of an acid. While the kind of acid is not particularly limited, for example, hydrohalic acids such as hydrofluoric acid, hydrochloric acid, hydrobromic acid, hydroiodic acid and the like; sulfonic acids such as methanesulfonic acid, benzenesulfonic acid, p-toluenesulfonic acid, trifluoromethanesulfonic acid and the like; carboxylic acids such as acetic acid, trifluoroacetic acid, benzoic acid and the like; sulfuric acid, nitric acid and the like can be mentioned. The amount of the acid to be used is preferably within the range of 0.1 to 10 molar equivalents, more preferably 0.5 to 3 molar equivalents, relative to 6-alkoxy-3,2'-bipyridine derivative (V).

The reaction can be carried out in the presence of water. The amount of water to be used is generally within the range of 0.5 to 100 molar equivalents, preferably 1 to 50 molar equivalents, relative to 6-alkoxy-3,2'-bipyridine derivative (V).

The reaction is preferably carried out within the range of 0° C. to 120° C., more preferably 20° C. to 100° C. The reaction time is generally within the range of 0.1-40 hr, preferably 0.5-20 hr.

The reaction can be carried out in the presence of a solvent. While the solvent is not particularly limited as long as it does not adversely affect the reaction, for example, aliphatic hydrocarbons such as hexane, heptane, octane and the like; aromatic hydrocarbons such as benzene, toluene, xylene, ethylbenzene, mesitylene, chlorobenzene and the like; ethers such as tetrahydrofuran, diethyl ether, diisopropyl ether, tert-butylmethyl ether, 1,2-dimethoxyethane, 1,4-dioxane, diglyme and the like; esters such as ethyl acetate, isopropyl acetate, butyl acetate and the like; nitriles such as acetonitrile, benzonitrile and the like; dimethylformamide, dimethyl sulfoxide and the like can be mentioned. The solvent may be used alone or in a combination of two or more kinds thereof. The amount of the solvent to be used is generally within the range of 0.5- to 50-fold weight, preferably 1- to 20-fold weight, relative to 6-alkoxy-3,2'-bipyridine derivative (V).

The 5-(2'-pyridyl)-2-pyridone derivative (VI) thus produced can be isolated or purified by the methods generally used for the isolation or purification of organic compounds. For example, the reaction mixture is washed with methyl-tert-butyl ether and the like, alkalified with sodium hydroxide and the like and then washed again with methyl-tert-butyl ether and the like. The aqueous solution containing the object product dissolved therein is neutralized, extracted with an organic solvent such as ethyl acetate and the like, the extract is concentrated and the obtained crude product is purified by silica gel chromatography, recrystallization and the like.

The pyridine derivative (I), which is the starting material, can be easily produced by, for example, a method comprising reacting industrially easily available 2-chloropyridine with sodium methoxide [Journal of the American Chemical Society, 46, 1466(1924)] and the like. In addition, 2-sulfonylpyridine derivative (IV) can be easily produced by, for example, a method comprising reacting α,β-unsaturated carbonyl compounds with sulfonyl cyanides (JP-A-11-269147).

EXAMPLES

The present invention is explained in detail by referring to Examples, which are not to be construed as limitative.

Example 1

Synthesis of 5-bromo-2-methoxypyridine

Ethyl acetate (325 kg), sodium acetate (58 kg, 707 mol) and 2-methoxypyridine (68.7 kg, 630 mol) were mixed in a reactor vessel (inner volume 1000 L). To this solution was added dropwise bromine (122.3 kg, 765 mol) over 6.5 hr while keeping the inside temperature from exceeding 10° C. After the dropwise addition, the inside temperature was raised to 20° C. and the mixture was stirred for 5 hr. The ratio of reaction progress at this time point was 73%. Thereafter, the inside temperature was raised to 50° C. and the reaction was continued more for 5 hr. The ratio of reaction progress at this time point was 98%. The reaction mixture was cooled and water (70 kg) was added to the reaction mixture. While keeping the inside temperature from exceeding 5° C., the solution obtained by dissolving sodium hydroxide (46.1 kg) and sodium sulfite (17 kg) in water (200 kg) was added dropwise. The reaction mixture was stood still to allow partitioning. After confirming that the pH of the aqueous layer was not less than 8 and peroxide was absent, the organic layer was separated. The aqueous layer was extracted with ethyl acetate (40 kg), and the extract and the above-mentioned organic layers were combined. The mixture was concentrated under reduced pressure to give crude 5-bromo-2-methoxypyridine (gross: 121.8 kg, net: 110.7 kg, yield 93%). The crude product was purified by distillation under reduced pressure to give 5-bromo-2-methoxypyridine (101.8 kg, yield 86%) having the following analytical data at a purity of not less than 99%.

$^1$H-NMR spectrum (CDCl$_3$) δ: 3.90(s, 3H), 6.65 (d, 1H, J=8.8 Hz), 7.62(dd, 1H, J=2.4 Hz, 8.8 Hz), 8.20(d, 1H, J=2.4 Hz)

Example 2

Synthesis of 6-methoxy-3,2'-bipyridine

Tetrahydrofuran (230 kg) was charged in a reactor vessel (inner volume 1000 L) and cooled to −76° C., after which a solution (15.2 wt %, 118 kg, 278 mol) of n-butyllithium in hexane was added therein. To this solution was added dropwise a solution obtained by dissolving 5-bromo-2-methoxypyridine (47.0 kg, 250 mol) in tetrahydrofuran (71 kg) over 3.5 hr at an inside temperature of −71° C. to −75° C. After the completion of the dropwise addition, the mixture was stirred for 1 hr and a sample was taken to confirm the disappearance of 5-bromo-2-methoxypyridine. To the obtained reaction mixture was added dropwise a solution obtained by dissolving 2-benzenesulfonylpyridine (45.7 kg, 209 mol) in tetrahydrofuran (133 kg) at a temperature range of −71° C. to −75° C. over 6.5 hr. After the completion of the dropwise addition, the mixture was stirred at −71° C. for 3 hr and isopropanol (32 kg) was added to stop the reaction.

The obtained reaction mixture was warmed to 0° C. and the reaction mixture was transferred to an extraction vessel containing water (216 kg) while keeping the inside temperature of the extraction vessel from exceeding 20° C. After the completion of the transfer, the mixture was stirred for 30 min, stood still and the organic layer was separated. The aqueous layer was extracted twice with ethyl acetate (82 kg+86 kg) and the extracts and the above-mentioned organic layer were combined and concentrated under reduced pressure to give a crude product (gross: 52.8 kg). The crude product was quantified and found to contain 36.8 kg (yield 95%, based on 2-benzenesulfonylpyridine) of 6-methoxy-3,2'-bipyridine having the following analytical data.

$^1$H-NMR spectrum (CDCl$_3$)δ: 4.00(s, 3H), 6.85(d, 1H, J=8.9 Hz), 7.20-7.24(m, 1H), 7.66(d, 1H, J=7.9 Hz), 7.74(dt, 1H, J=2.0 Hz, 7.9 Hz), 8.25(dd, 1H, J=2.0 Hz, 8.9 Hz), 8.66-8.68(m, 1H), 8.74(d, 1H, J=2.0 Hz)

Example 3

Synthesis of 5-(2'-pyridyl)-2-pyridone

Crude 6-methoxy-3,2'-bipyridine (55.0 kg, net: 42.6 kg) obtained in Example 2, 35% hydrochloric acid (65 kg) and water (110 kg) were charged in a reactor vessel (inner volume 500 L) and the mixture was heated under reflux for 4 hr. The reaction mixture was cooled and the aqueous layer was washed with methyl-tert-butyl ether (116 kg×4). A solution obtained by dissolving sodium hydroxide (35 kg) in water (102 kg) was added while maintaining the inside temperature at 25-35° C. to adjust its pH to 12, and the aqueous layer was washed again with methyl-tert-butyl ether (116 kg×2). 35% Hydrochloric acid (40 kg) was added while maintaining the inside temperature at 25-40° C. to adjust its pH to 7. This mixture was transferred to a reactor vessel (inner volume 1000 L), n-butanol (175 kg) was added and sodium chloride (70 kg) was further added. The organic layer was separated and the aqueous layer was extracted with n-butanol (175 kg). The extract and the organic layer were combined and concentrated until n-butanol remaining in the reactor vessel became 69 kg. Ethyl acetate (84 kg) was added to the concentrate, and the mixture was dissolved by heating to 80° C. and cooled to 0° C. to allow recrystallization to give crude 5-(2'-pyridyl)-2-pyridone (32.1 kg, net: 29.1 kg). This was added to water (224 kg), dissolved by heating to 60° C. and cooled to 0° C. The obtained slurry was filtered, washed with water (45 kg) and dried to give 5-(2'-pyridyl)-2-pyridone (23.56 kg, yield 60%).

$^1$H-NMR spectrum (CDCl$_3$) δ: 6.72(d, 1H, J=9.9 Hz), 7.19 (dd, 1H, J=4.9 Hz, 6.9 Hz), 7.51(d, 1H, J=7.9 Hz), 7.70-7.76 (m, 1H), 8.15-8.23(m, 2H), 8.62(d, 1H, J=4.0 Hz), 13.30(brs, 1H)

INDUSTRIAL APPLICABILITY

According to the present invention, 5-(2'-pyridyl)-2-pyridone derivative (VI) can be advantageously produced industrially.

This application is based on application No. 2002-214098 filed in Japan, the contents of which are incorporated hereinto by reference.

The invention claimed is:

1. A production method of a 5-(2'-pyridyl)-2-pyridone compound represented by the formula (VI)

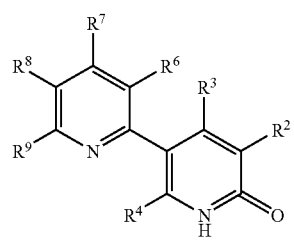

wherein
R$^2$, R$^3$ and R$^4$
are each a hydrogen atom, an alkyl group optionally having substituent(s), an aryl group optionally having substituent(s), an alkoxy group optionally having substituent(s) or an aryloxy group optionally having substituent(s), or R$^2$ and R$^3$ optionally form, together with a carbon atom bonded thereto, a ring optionally having substituent(s), and R$^6$, R$^7$, R$^8$ and R$^9$
are each a hydrogen atom, an alkyl group optionally having substituent(s) or an aryl group optionally having substituent(s), or R$^6$ and R$^7$, R$^7$ and R$^8$, or R$^8$ and R$^9$ optionally form, together with a carbon atom bonded thereto, a ring optionally having substituent(s), which comprises reacting a pyridine compound represented by the formula (I)

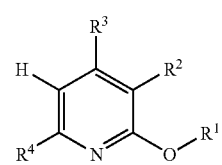

wherein R$^1$ is an alkyl group optionally having substituent(s) or an aryl group optionally having substituent(s), and R$^2$, R$^3$ and R$^4$ are as defined above, with a brominating agent to give a 5-bromopyridine compound represented by the formula (II)

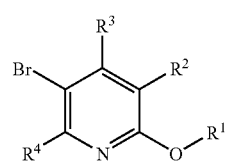

wherein R$^1$, R$^2$, R$^3$ and R$^4$ are as defined above, reacting the obtained 5-bromopyridine compound (II) with a metallizing agent to give an organometallic compound represented by the formula (III)

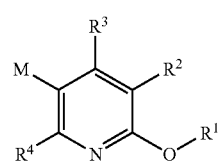

wherein M is a metal atom belonging to group 1 of the periodic table, and R$^1$, R$^2$, R$^3$ and R$^4$ are as defined above, reacting the obtained organometallic compound (III) with a 2-sulfonylpyridine compound represented by the formula (IV)

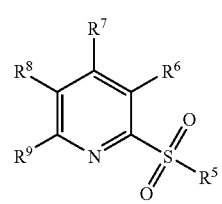

wherein R$^5$ is an alkyl group optionally having substituent(s) or an aryl group optionally having substituent(s), and $R^6$, $R^7$, $R^8$ and $R^9$ are as defined above, to give a 6-alkoxy-3,2'-bipyridine compound represented by the formula (V)

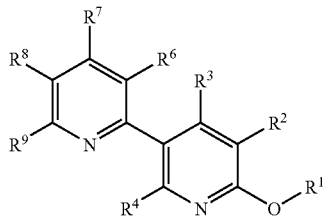
(V)

wherein $R^1$, $R^2$, $R^3$, $R^4$, $R^6$, $R^7$, $R^8$ and $R^9$ are as defined above, and hydrolyzing the obtained 6-alkoxy-3,2'-bipyridine compound (V).

2. The production method of claim 1, wherein the organometallic compound is a compound of the formula (III) wherein M is a lithium atom.

3. The production method of claim 1 or 2, wherein, in the formula (VI), $R^2$, $R^3$, $R^4$, $R^6$, $R^7$, $R^8$ and $R^9$ are each a hydrogen atom.

4. The production method of claim 1 or 2, wherein, in the formula (I), $R^1$ is a methyl group.

5. The production method of claim 1 or 2, wherein, in the formula (IV), $R^5$ is a phenyl group.

6. The production method of claim 1, wherein the metallizing agent is an n-butyllithium.

7. The production method of claim 1, wherein the brominating agent is a bromine.

8. The production method of claim 1,
wherein
$R^2$, $R^3$, $R^4$, $R^6$, $R^7$, $R^8$ and $R^9$ of the formula (VI) are each a hydrogen atom,
$R^1$ of the formula (I) is a methyl group;
the brominating agent is a bromine;
the metallizing agent is an n-butyllithium;
the organometallic compound is a compound of the formula (III) wherein M is a lithium atom; and
$R^5$ of the formula (IV) is a phenyl group.

9. The production method of claim 1, wherein said pyridine compound of formula (I) is reacted at a temperature of 0 to 80° C.

10. The production method of claim 1, wherein said pyridine compound of formula (I) is reacted in the presence of a base.

11. The production process of claim 1, further comprising isolation of said 5-bromopyridine compound (II).

12. The production process of claim 1, wherein said metallizing agent is at least one selected from the group consisting of an alkyl lithium compound, a Grignard reagent, lithium, magnesium and sodium.

13. The production process of claim 1, wherein reacting said 5-bromopyridine compound (II) is conducted in at least one solvent selected from the group consisting of an aliphatic hydrocarbon, an aromatic hydrocarbon and an ether.

14. The production process of claim 1, wherein said 2-sulfonylpyridine compound (IV) is added to a reaction mixture containing said organometallic compound (III).

15. The production process of claim 1, wherein a reaction mixture containing said organometallic compound (III) is added to a solution comprising said 2-sulfonylpyridine compound (IV).

16. The production process of claim 14, wherein said 2-sulfonylpyridine compound (IV) is added as a concentration of 1-80 wt. in a solvent.

17. The production process of claim 1, wherein said 6-alkoxy-3-2'-bipyridine compound (V) is hydrolyzed without isolation and purification.

18. The production process of claim 1, wherein said 6-alkoxy-3-2'-bipyridine compound (V) is hydrolyzed in the presence of an acid.

* * * * *